(12) United States Patent
Buehlmann et al.

(10) Patent No.: US 7,150,712 B2
(45) Date of Patent: Dec. 19, 2006

(54) TARGET TISSUE LOCALIZATION ASSEMBLY AND METHOD

(76) Inventors: Eric L. Buehlmann, 568 California Way, Redwood City, CA (US) 94062; Robert J. Laird, 2325 Monte Vista Ave., Pinole, CA (US) 94564; William R. Dubrul, One Uccelli Blvd., Redwood City, CA (US) 94063

( * ) Notice: Subject to any disclaimer, the term of this patent is extended or adjusted under 35 U.S.C. 154(b) by 712 days.

(21) Appl. No.: 10/212,467

(22) Filed: Aug. 5, 2002

(65) Prior Publication Data
US 2004/0049224 A1      Mar. 11, 2004

Related U.S. Application Data

(63) Continuation of application No. 10/039,750, filed on Nov. 7, 2001, now abandoned.

(60) Provisional application No. 60/246,413, filed on Nov. 7, 2000.

(51) Int. Cl.
*A61B 1/00*     (2006.01)

(52) U.S. Cl. ........................ 600/114; 600/567

(58) Field of Classification Search ................ 600/114, 600/115, 567, 562, 564, 570
See application file for complete search history.

(56) References Cited

U.S. PATENT DOCUMENTS

| | | |
|---|---|---|
| 3,557,794 A | 1/1971 | Van Patten |
| 3,910,279 A | 10/1975 | Okada |
| 3,996,938 A | 12/1976 | Clark, III |
| 4,638,802 A | 1/1987 | Okada |
| 5,007,908 A | 4/1991 | Rydell |
| 5,030,201 A | 7/1991 | Palestrant |
| 5,275,610 A | 1/1994 | Eberbach |
| 5,370,660 A | 12/1994 | Weinstein et al. |
| 5,417,697 A | 5/1995 | Wilk |
| 5,709,697 A | 1/1998 | Ratcliff |
| 5,794,626 A | 8/1998 | Kieturakis |
| 5,795,308 A | 8/1998 | Russin |
| 5,928,159 A | 7/1999 | Eggers |
| 5,928,260 A | 7/1999 | Chin et al. |
| 5,954,742 A | 9/1999 | Osypka |
| 5,989,265 A | 11/1999 | Bouquet De La Joliniere |
| 6,022,362 A | 2/2000 | Lee |
| 6,033,398 A | 3/2000 | Farley |
| 6,051,008 A | 4/2000 | Saadat |
| 6,053,876 A | 4/2000 | Fisher |
| 6,059,734 A | 5/2000 | Yoon |
| 6,106,524 A | 8/2000 | Eggers |
| 6,179,860 B1 | 1/2001 | Fulton |

(Continued)

FOREIGN PATENT DOCUMENTS

WO      WO 9502370      1/1995

(Continued)

OTHER PUBLICATIONS

EPO Search Report dated Jul. 6, 2005 for EPO Application No. EP 01273413.3.

(Continued)

*Primary Examiner*—Beverly M. Flanagan (57) ABSTRACT

A target tissue localization assembly includes a radially expandable tissue anchor connected to the distal ends of an anchor assembly and an elongated anchor actuator element. A lock, engageable between the actuator element and the placement element, may be used to prevent collapse of the anchor from its radially expanded state. A sheath may be slidably mounted over the anchor assembly. The sheath and the anchor assembly may be configured to permit the sheath to move in a proximal direction, relative to the anchor assembly, past a chosen location while preventing the sheath from moving past the chosen location in a distal direction.

54 Claims, 6 Drawing Sheets

U.S. PATENT DOCUMENTS

| | | |
|---|---|---|
| 6,221,006 B1 | 4/2001 | Dubrul |
| 6,261,241 B1 | 7/2001 | Burbank |
| 6,277,083 B1 | 8/2001 | Eggers |
| 6,287,304 B1 | 9/2001 | Eggers |
| 6,312,428 B1 | 11/2001 | Eggers |
| 6,312,429 B1 | 11/2001 | Burbank et al. |
| 6,331,166 B1 | 12/2001 | Burbank et al. |
| D457,628 S | 5/2002 | Eggers |
| D457,960 S | 5/2002 | Eggers |
| 6,432,103 B1 | 8/2002 | Ellsberry |
| 6,440,147 B1 | 8/2002 | Lee |
| 6,471,659 B1 | 10/2002 | Eggers |
| 6,514,248 B1 | 2/2003 | Eggers |
| 6,430,923 B1 | 3/2003 | Fulton |
| 6,540,693 B1 | 4/2003 | Burbank |
| 6,602,204 B1 | 8/2003 | Dubrul |
| 6,620,157 B1 | 9/2003 | Dabney |
| 6,626,903 B1 | 9/2003 | McGuckin |
| 2002/0007130 A1 | 1/2002 | Burbank et al. |

FOREIGN PATENT DOCUMENTS

| | | |
|---|---|---|
| WO | WO 9939648 | 8/1999 |
| WO | WO 0010471 | 3/2000 |
| WO | WO 0074561 | 12/2000 |
| WO | WO 0205717 | 1/2002 |
| WO | WO 04075732 | 9/2004 |
| WO | WO 04075947 | 9/2004 |

OTHER PUBLICATIONS

PCT Search Report dated Sep. 5, 2002 for PCT Application No. PCT/US01/50380.

PCT Search Report dated Jan. 30, 2003 for PCT Application No. PCT/US01/50978.

PCT Search Report dated Apr. 20, 2005 for PCT Application No. PCT/US2004/005070.

TARGET TISSUE LOCALIZATION ASSEMBLY AND METHOD

CROSS REFERENCE TO OTHER APPLICATIONS

This application is a Continuation of U.S. application Ser. No. 10/039,750 filed 7 Nov. 2001, now abandoned, and claims the benefit of U.S. Provisional Patent Application No. 60/246,413 filed 7 Nov. 2000 and entitled Tissue Therapy and/or Removal Apparatus and Methods for Use. See also: (1) U.S. Pat. No. 6,179,860 issued 30 Jan. 2001 and entitled Target Tissue Localization Device And Method, (2) International Publication No. WO 00/10471 published 2 Mar. 2000 and entitled Target Tissue Localization Device And Method, (3) U.S. Pat. No. 6,221,006 issued 24 Apr. 2001 and entitled Entrapping Apparatus And Method For Use, (4) International Publication No. WO 99/39648 published 12 Aug. 1999 and entitled Entrapping Apparatus And Method For Use, (5) U.S. patent application Ser. No. 09/588,278 filed 5 Jun. 2000 and entitled Tissue Removal Methods And Apparatus, and (6) International Publication No. WO 00/74561 published 14 Dec. 2000 and entitled Tissue Removal Methods And Apparatus.

BACKGROUND OF THE INVENTION

In the U.S. alone approximately one million women will have breast biopsies because of irregular mammograms and palpable abnormalities. Biopsies can be done in a number of different ways for non-palpable lesions, including surgical excisional biopsies and stereotactic and ultrasound guided needle breast biopsies. In the case of image directed biopsy, the radiologist or other physician takes a small sample of the irregular tissue for laboratory analysis. If the biopsy proves to be malignant, additional surgery (typically a lumpectomy or a mastectomy) is required. In the case of needle biopsies, the patient then returns to the radiologist a day or two later where the biopsy site (the site of the lesion) is relocated by method called needle localization, a preoperative localization in preparation for the surgery.

Locating the previously biopsied area after surgical excision type of biopsy is usually not a problem because of the deformity caused by the surgery. However, if the biopsy had been done with an image directed needle technique, as is common, help in relocating the biopsy site is needed. One procedure to permit the biopsy site to be relocated by the radiologist during preoperative localization is to leave some of the suspicious calcifications; this has its drawbacks.

Another way to help the radiologist relocate the biopsy site involves the use of a small metallic surgical clip, such as those made by Biopsys. The metallic clip can be deployed through the biopsy needle, and is left at the biopsy site at the time of the original biopsy. With the metallic clip as a guide, the radiologist typically inserts a barbed or hooked wire, such as the Hawkins, Kopans, Homer, Sadowski, and other needles, back into the patient's breast and positions the tip of the wire at the biopsy site using mammography to document the placement. The patient is then taken to the operating room with the needle apparatus sticking out of the patient's breast. While the clip provides a good indication of the biopsy site to the radiologist during preoperative localization, the clip remains permanently within the 80% of patients with benign diagnoses. Also, because the clip is necessarily attached to a single position at the periphery of the biopsy site, rather than the center of the biopsy site, its location may provide a misleading indication of the location of diseased tissue during any subsequent medical intervention. The clip is also relatively expensive. In addition, the soft nature of breast tissue permits the tip of the barbed or hooked needle to be relatively easily dislodged from the biopsy site. The surgeon typically pulls on the needle to help locate the area to be removed. This pulling motion during the excision may be responsible more than any other single factor for the movement of the needle. Additionally, these devices are not easily felt by external palpation and the tip is difficult to locate without dissection into the tissues; this prevents a surgical approach which may be more cosmetically advantageous and surgically appropriate than dissecting along the tract of the needle.

Another localization method involves the use of laser light from the tip of a optical fiber connected to a laser. A pair of hooks at the tip of the optical fiber secures the tip at the biopsy site; the glow indicates the position of the tip through several centimeters of breast tissue. This procedure suffers from some of the same problems associated with the use of barbed or hooked wires. Another preoperative localization procedure injects medical-grade powdered carbon suspension from the lesion to the skin surface. This procedure also has certain problems, including the creation of discontinuities along the carbon trail.

SUMMARY OF THE INVENTION

One aspect of the present invention is directed to a target tissue localization assembly including an anchor assembly comprising an elongated placement element, an elongated anchor actuator element, typically a wire, and a radially expandable tissue anchor, typically made of a tubular mesh material. The placement element may be stiff or flexible along all or part of its length. In one embodiment of the placement element is a stiff hollow shaft. The anchor is movable from a radially contracted condition to a radially expanded, deployed condition when the distal ends of the placement element and actuator element are moved relative to one another. A lock is engageable between the actuator element and the placement element when the anchor is in the deployed condition to at least temporarily prevent collapse of the anchor. The assembly may also include a sheath slidably mounted over the anchor assembly. The sheath may include a hub mounted to the proximal end of the sheath.

Another aspect of the invention is directed to a target tissue localization assembly including an elongated placement element, an elongated anchor actuator element and a radially expandable tissue anchor. A movement-limiting element is engageable between the placement element and a proximal portion of the anchor to at least hinder proximal movement of the proximal anchor portion when the actuator element is pulled proximally so to permit radially expansion of the anchor to a deployed condition. Locking means at least temporarily prevents collapse of the anchor when the anchor is in the deployed condition.

A further aspect of the invention is directed to a target tissue localization assembly including anchor assembly means for locating a tissue anchor at a target site and selectively expanding the anchor. Locking means at least temporarily prevents the anchor from moving from a radially expanded state to a radially contracted state.

Another aspect of the invention is directed to a method for localizing target tissue at a target site of a patient. The method includes percutaneously positioning the tip of an anchor assembly at or near a target site of the patient; the anchor assembly includes an elongated placement element, such as a hollow shaft, an elongated anchor actuator element, such as a wire, extending along the placement element, and a radially expandable tissue anchor, such as one made of a tubular mesh material, connected to the placement and anchor actuator elements. The anchor is placed in a radially expanded condition by moving at least portions of the anchor actuator and placement elements relative to one another in a first direction. Movement of the portions of the anchor actuator and placement elements relative to one another in a second direction is at least temporarily prevented so to maintain the anchor in the radially expanded condition.

A further aspect of the present invention is directed to a target tissue localization assembly including an anchor assembly comprising an elongated placement element, typically a stiff or flexible hollow shaft, an elongated anchor actuator element, typically a wire, and a radially expandable tissue anchor, typically made of a tubular mesh material. The anchor is movable from a radially contracted condition to a radially expanded, deployed condition when the distal ends of the placement element and actuator element are moved relative to one another. A sheath is slidably mounted over the anchor assembly. A chosen one of one of the placement element and the sheath comprises a surface interruption, such as a groove shoulder in the placement element, at a first location along said the chosen one. The other on the placement element and the sheath comprises a surface interruption engagement element, such as a clip, at a second position along said the other. The surface interruption and engagement elements are configured to (a) permit the surface interruption engagement element to move past the surface interruption in a first direction but (b) not permit the surface interruption engagement element to move past the surface interruption in a second direction opposite the first direction. The sheath may include a hub and the surface interruption engagement element may be a clip carried by the hub. The clip may include a spring finger which frictionally engages the placement element and permits the hub to move in a proximal direction past the shoulder (or other surface interruption) while preventing the hub from moving past the shoulder in a distal direction.

Another aspect of the invention is directed to a target tissue localization assembly including anchor assembly means for locating a tissue anchor at a target site and selectively expanding the anchor and sheath means slidably mounted over the anchor assembly means. The assembly also includes means for (a) permitting a first location along the sheath means to move in a first direction past a second location along the anchor assembly means while (b) preventing the first location from moving past the second location in a second direction opposite the first direction.

A still further aspect of the invention is directed to a method for localizing target tissue at a target site of the patient. The method includes percutaneously positioning the tip of an anchor assembly, slidably housed within a sheath assembly, at or near a target site of the patient; the anchor assembly includes an elongated placement element, such as a hollow shaft, an elongated anchor actuator element, such as a wire, extending along the placement element, and a radially expandable tissue anchor, such as one made of a tubular mesh material, connected to the placement and anchor actuator elements. The sheath assembly is maintained at a fixed position relative to the patient following the positioning step. Proximal movement of the placement element relative to the sheath assembly is prevented. The anchor is placed in a radially expanded condition by moving the anchor assembly relative to the placement element.

Other features and advantages of the invention will appear from the following description in which the specific embodiments have been set forth in detail in conjunction with the accompanying drawings.

DESCRIPTION OF THE SPECIFIC EMBODIMENTS

A target tissue localization assembly 10 is shown in FIGS. 1A–2D to include an anchor assembly 12 comprising an elongated placement element in the form of a stiff tubular shaft 14, an elongated anchor actuator element in the form of an actuator wire 16, and a radially expandable tissue anchor in the form of a tubular mesh anchor 18 mounted to the distal ends 20, 22 of shaft 14 and wire 16, respectively. Assembly 10 also includes a sheath assembly 24, including a sheath 26 and a hub 28 rigidly secured to the proximal end of sheath 26, slidably mounted over anchor assembly 12, a lock 30 having a proximal end 32 fixed to the proximal end of 34 of wire 16, and a handle 36 slidably mounted over the proximal end of anchor assembly 12.

Figure 1A:
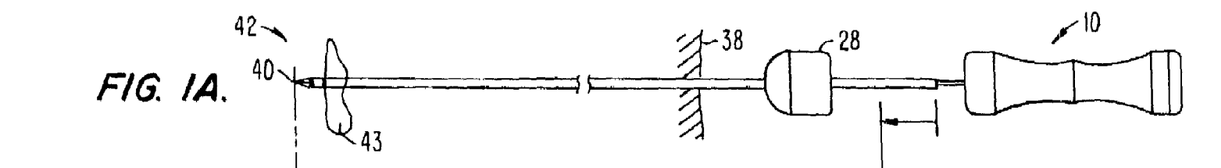
FIG. 1A illustrates a target tissue localization assembly made according to the invention with the tip of the anchor assembly at a target site within a patient's breast.
Figures 1B, 1C:
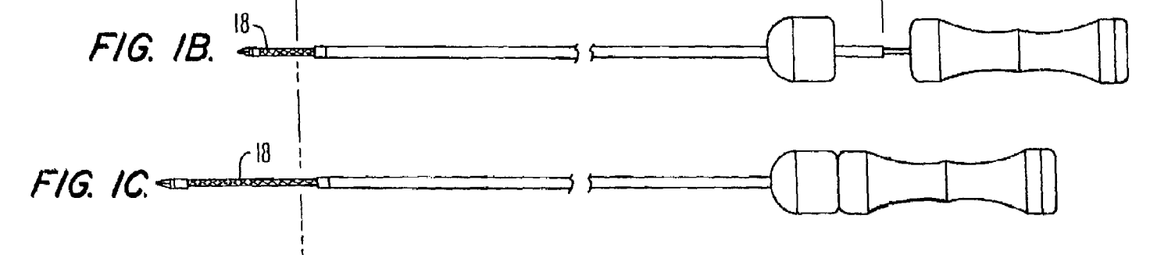
FIG. 1B illustrates the assembly of FIG. 1A showing the initial distal movement of the handle relative to the sheath assembly with the anchor partially extended.
FIG. 1C shows the assembly of FIG. 1B with the anchor fully extended.
Figures 1D, 1E:
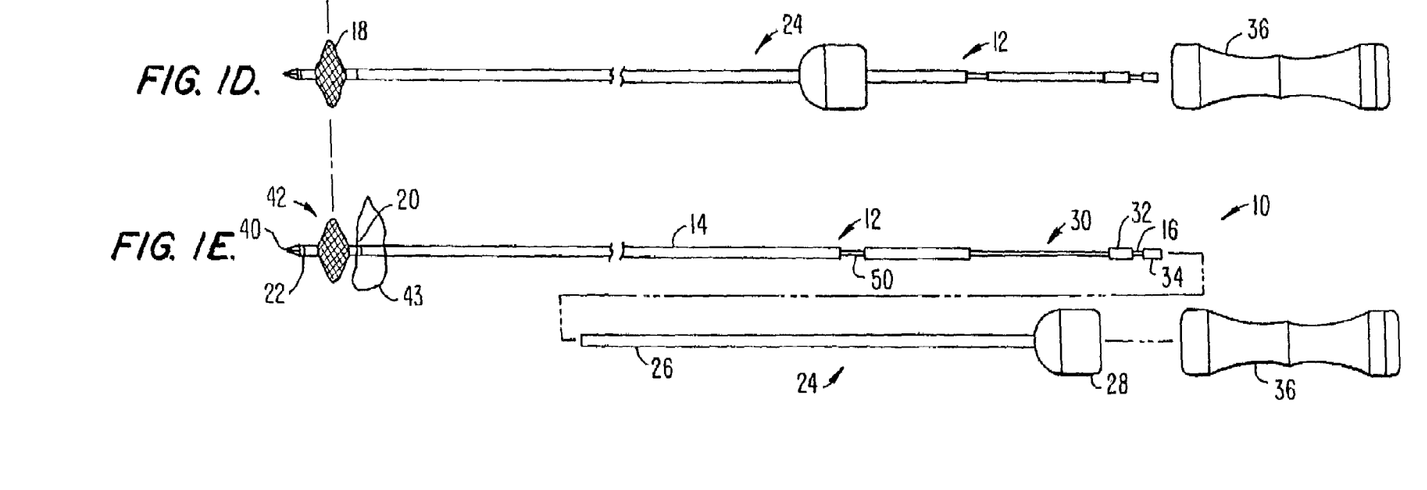
FIG. 1D shows a result of pulling the handle proximally causing the anchor to move through its radially expanded, deployed condition.
FIG. 1E illustrates the assembly of FIG. 1D with the sheath assembly removed.
Figure 2A:
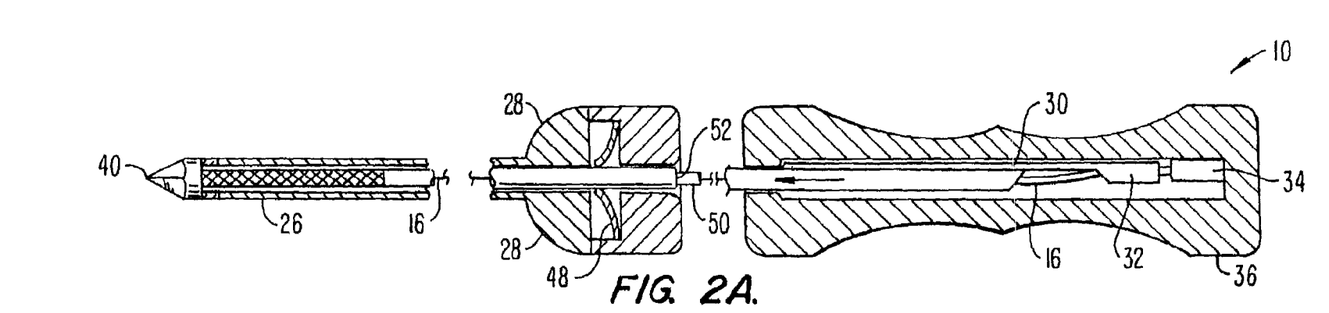
FIGS. 2A and 2B are enlarged cross-sectional views of portions of the assembly of FIGS. 1A and 1C.
Figure 2B:
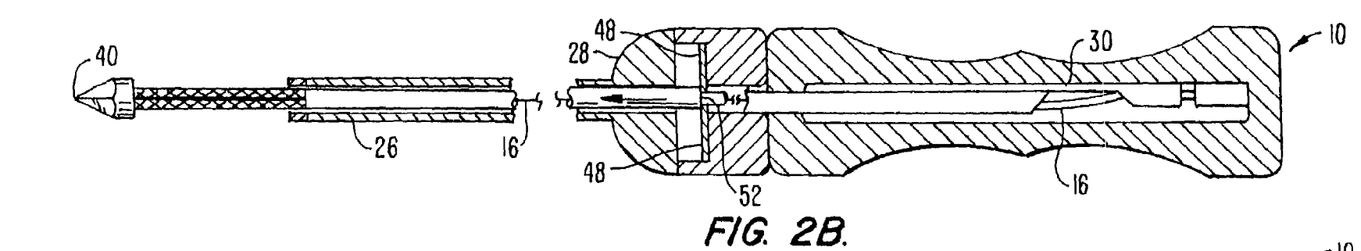
Figure 2C:
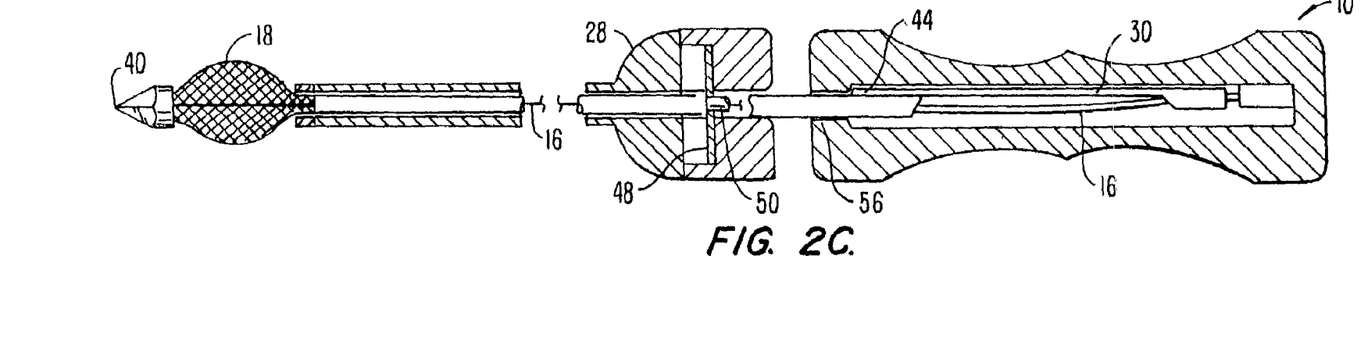
FIG. 2C illustrates the structure of FIG. 2B after the handle has been pulled a short distance to partially expand the anchor.
Figure 2D:
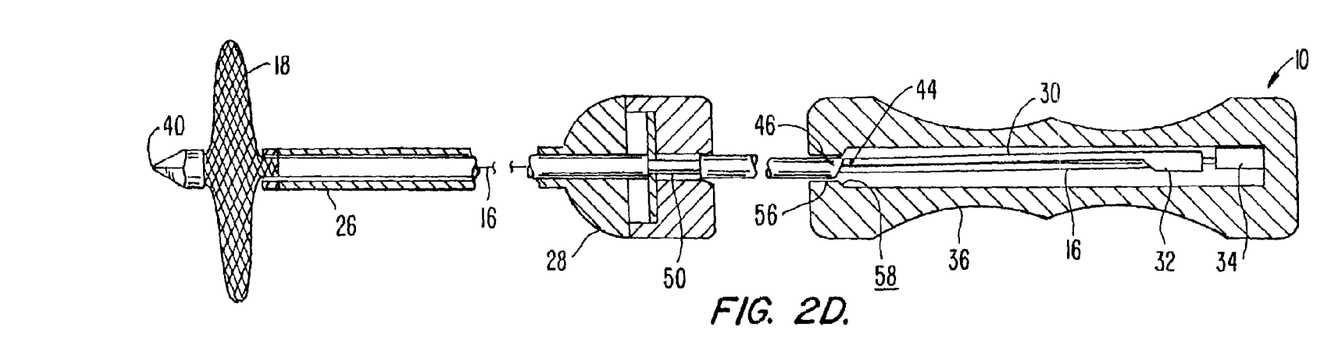
FIG. 2D shows the structure of FIG. 2C with the anchor fully deployed and locked in its fully deployed condition.
Figure 2E:
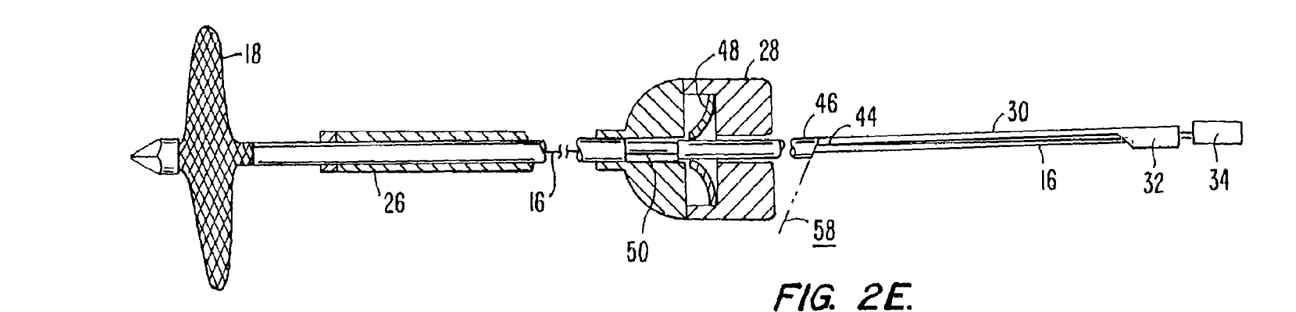
FIG. 2E illustrates the structure of FIG. 2D after the handle has been removed and showing the sheath assembly being pulled proximally during removal of the sheath assembly.

The actuation sequence for FIGS. 1A–2D is generally as follows. FIGS. 1A/2A show the assembly with the distal portion of assembly 10 passing percutaneously through the skin 38 of a patient's breast with the tip 40 of anchor assembly 12 positioned at a target site 42. FIG. 1B shows tubular mesh anchor 18 partially extended. FIGS. 1C/2B show the full extension of tubular mesh anchor 18, still in its radially contracted condition. FIG. 2C shows tubular mesh anchor 18 partially radially expanded. FIG. 2D shows handle 36 moved proximally causing the distal end 44 of lock 30 to engage the proximal end 46 of tubular shaft 14 to lock anchor 18 in its radially expanded, deployed condition. FIG. 1D shows handle 36 removed with anchor 18 in still locked in its axially expanded, deployed condition. FIG. 2E shows sheath assembly 24 being removed from anchor assembly 12. FIG. 1E shows sheath assembly 24 and handle 36 completely removed from anchor assembly 12.

Tip 40 is typically passed through and placed distally of target lesion 43, shown in FIGS. 1A and 1E only, with anchor 18 housed within shaft 14. While assembly 10 could be designed so that tip 40 is positioned proximally of target lesion 43 prior to extension of anchor 18, this would require that the tubular mesh anchor 18, as shown in FIGS. 1B and 1C, pass through the target lesion. This would likely be more difficult than the distal positioning because of the loss of the columnar strength that shaft 14 provides when passing through target lesion 43, especially since the target lesion is typically firmer than the surrounding tissue and thus more difficult to penetrate. Also, pushing anchor 18 through target lesion 43 may result in the seeding of a portion of the tissue track with particles of target lesion 43; such seeding is much less likely when anchor 18 is covered by shaft 14.

In the disclosed embodiment anchor 18 tends to radially expand in a symmetrical manner to create an anchor with a round cross-sectional shape. However, anchor 18 could expand radially to create an anchor which is not symmetrical and may expand, for example, to one side of shaft 14 only.

The placement of sharpened tip 40 of anchor assembly 12 at target site 42 occurs with tip 40 adjacent to distal end 20 of anchor assembly 12 to provide for smooth passage through the skin 38 and to the target site. This typically occurs with the aid of remote sensing techniques, such as x-ray, MRI, mammography or ultrasound. To aid such remote sensing, appropriate portions of assembly 10, in particular tip 40, can be made to be radiopaque, echoic, etc. according to the remote sensing technique used. As indicated in FIGS. 1A-1E, the position of anchor 18 is the same as the position of tip 40, that is at target site 42; this is achieved by not moving sheath assembly 24 relative to skin 38 and by the sizing and configuration of anchor 18. The movement of handle 36 from the position of FIG. 1A to the position of FIG. 1B causes anchor assembly 12 to slide through sheath assembly 24. See also FIGS. 2A and 2B. By the time anchor 18 is fully extended, as shown in FIGS. 2B and 1C, a locking clip 48, see FIG. 3, has moved over the outer surface of tubular shaft 14 and entered a groove 50 formed in shaft 14 so to lie against a shoulder 52 defined by the groove. The placement and configuration of shoulder 52 and clip 48, with its radially inward extending spring fingers 54, prevents the reverse movement of sheath assembly 24, that is the movement of sheath assembly 24 in a distal direction relative to anchor assembly 12. This is important because it allows the physician or technician to stabilize the position of tubular shaft 14 within the patient as wire 16 is pulled proximally by the proximal movement of handle 36 as illustrated in FIGS. 2C–2D. This proximal movement of wire 16 occurs because the reduced diameter portion 56 of handle 36 engages distal end 44 of lock 30 when pulled proximally. The distal end 44 of lock 30 automatically moves into engagement with proximal end 46 of shaft 14 because of both the resilient character of lock 30 and the angled surface 58 of portion 56. The distal and proximal ends 44, 46 define an angled plane 60 which lies an acute angle to the longitudinal axis of tubular shaft 14 to help keep ends 44, 46 engaged. The anchor 18 may be partially or fully contracted by disengaging ends 44, 46 to permit wire 16 to move in a distal direction through shaft 14. This may be useful when, for example, it is desired to reposition anchor 18.

Once anchor 18 is in its radially expanded, deployed condition, handle 36 maybe removed as suggested in FIG. 1D, followed by the removal of sheath assembly 24 if such removal is desired. Anchor 18 is typically positioned distally of a target lesion 60, or other target tissue, and provides a stable localization device to help identify the location of lesion 60 for therapeutic or diagnostic procedures, including invasive and relatively noninvasive surgical procedures. Access to target lesion 60 is typically along the tissue tract created by assembly 10; access may be from a different direction, such as long a supplemental surgical access path generally perpendicular to the tissue tract. In such situations it may be useful to use an anchor assembly 12 that is quite flexible to aid removal of target lesion 60 and anchor assembly 12 along the supplemental surgical access path.

It is presently contemplated that handle 36 will be a reusable, sterilizable component of assembly 10. Anchor assembly 12 and sheath assembly 24 may be supplied in sterilized packaging to permit a sterile handle 36 to be mounted on to anchor assembly 12 from tip 40, after which sheath assembly 24 is mounted on anchor assembly 12 from the tip. While it is not presently contemplated that anchor assembly 12 will be reusable, it may be that sheath assembly 24 may be constructed to be reusable after proper sterilization.

Anchor 18 is, in the disclosed embodiment, a tubular braided mesh which when collapsed axially, expands radially as shown in the figures. It may be desired to use an anchor that is self expanding. In either event, according to one aspect of the invention, it is desired that the assembly be constructed so that after partially or fully radially expanding anchor 18, the anchor may be partially or fully radially collapsed to permit the anchor to be repositioned within the body. Also, anchor 18 may be other than a mesh material, such as a malecot structure.

Assembly 10 is preferably in the made of sterilizable, biocompatible materials, whether conventional or unconventional. For example, shaft 14, sheath 26, anchor 18, wire 16 and lock 30 may be made of stainless steel, or other suitable metal or non-metal, while handle 36 and hub 28 may be made of a polymer such as polycarbonate. If sheath assembly 24 and/or handle 36 is to be autoclaved (typically because it is to be reused), a material capable of withstanding autoclaving, such as a metal or a non-metal such as ABS, Ultem® or Delrin®, should be used.

Figure 3:
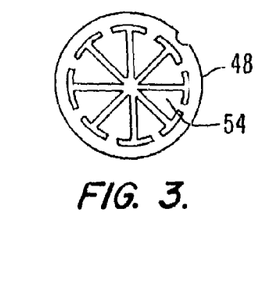
FIG. 3 is a front view of the clip of FIGS. 2A–2E.
Figure 4:
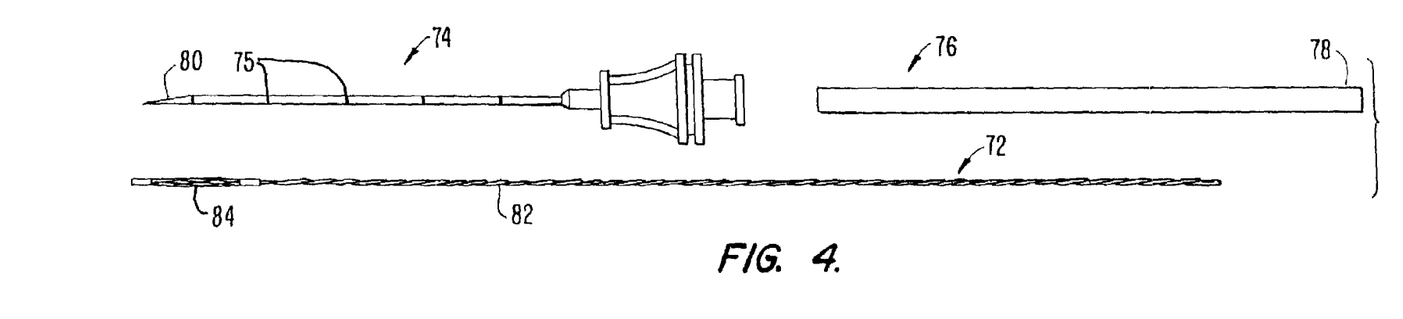
FIG. 4 is an exploded view of an alternative embodiment of the target tissue localization assembly of FIGS. 1A–1E.
Figure 4A:
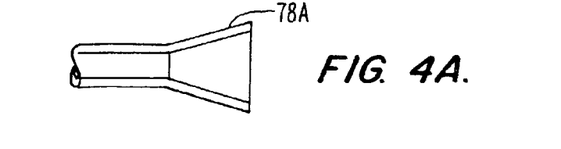
FIG. 4A is an enlarged cross-sectional view of an alternative embodiment of the proximal end of the protective cover of FIG. 4.
Figure 5:
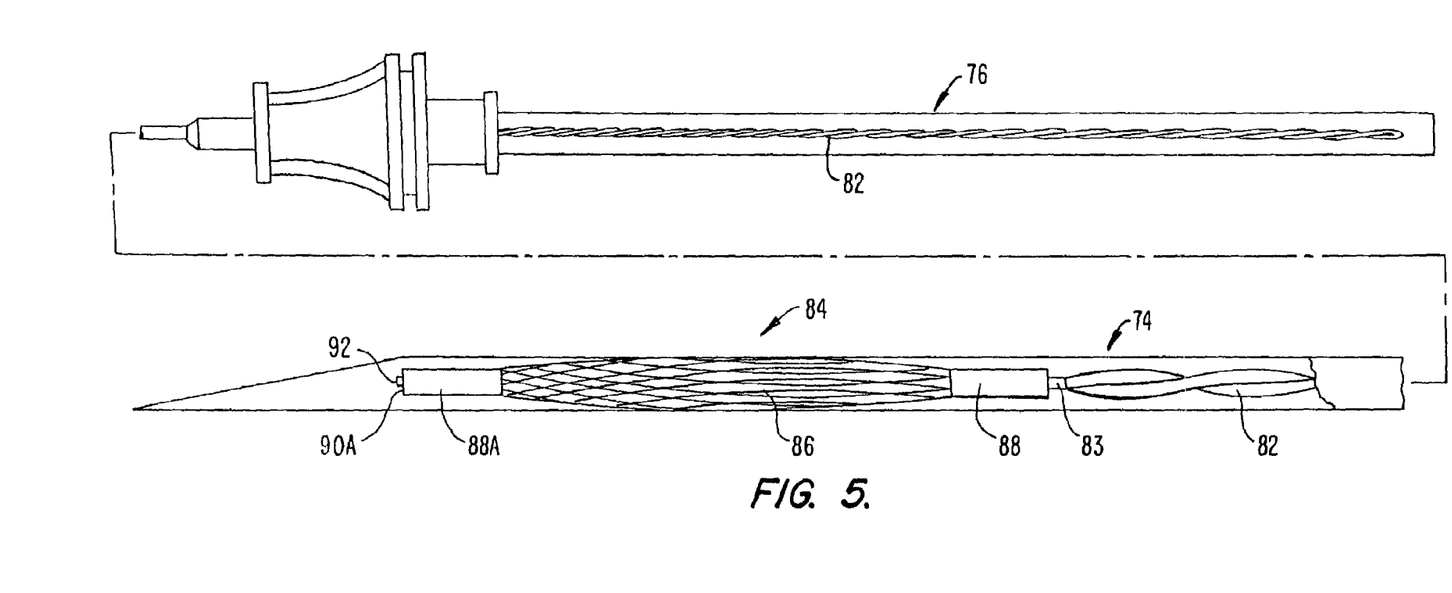
FIG. 5 is an assembled, partial cross-sectional view of the assembly of FIG. 4 with the distal portion enlarged to show detail.

FIGS. 4 and 5 illustrate an alternative embodiment of the invention similar to but generally simpler than the embodiment shown in FIGS. 1–3. Target tissue localization assembly 70 is shown to include an anchor assembly 72 slidably housed within a hollow placement element 74. Placement element 74 has radiopaque markings 75 along its length to aid proper placement. A hollow protective cover 76 may be used to house all or part of anchor assembly 72 for shipment and storage. Protective cover 76 may be constructed to act as a conduit to permit a fluid, such as from a syringe, to be introduced to the target site through placement element 74. The proximal end 78 of cover 76 may be especially adapted to facilitate a fluid coupling; one such configuration is shown in FIG. 4A as end 78A.

Figure 6:
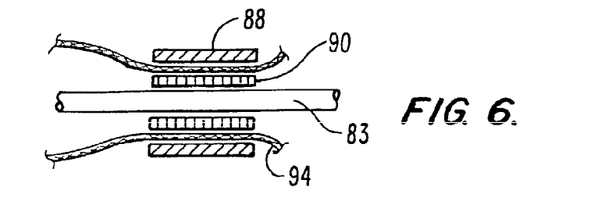
FIG. 6 is an enlarged cross-sectional view of the proximal portion of the tissue anchor of FIG. 5.

Placement element 74 acts as a hollow needle and serves the functions of both shaft 14 and sheath 26. As shown in the figures, its distal end 80 is sharpened to facilitate passage through tissue. Anchor assembly 72 comprises a flexible anchor actuator element 82, preferably consisting of a twisted wire, and a braided tissue anchor 84. Tissue anchor 84 comprises a braided tubular mesh material 86, the ends of which are captured between concentrically arranged outer and inner sleeves 88, 90 and 88A, 90A; sleeves 88, 90 are shown in FIG. 6. Material 86 is preferably secured between sleeves 88, 90 and between sleeves 88A, 90A by an adhesive; others securing schemes, such as soldering, gluing or crimping, could also be used. As shown in FIGS. 5 and 6, the twisted wire anchor actuator element 82 becomes a single strand portion 83 as it passes through tissue anchor 84. Portion 83 passes freely through proximal sleeves 88, 90. Sleeves 88A, 90B are securely crimped onto distal end 92 of element 82. It may be desirable to use only sleeve 88A at the distal end of anchor 84 and secure material 86 directly between sleeve 88A and element 82 by crimping.

The stiffness of actuator element 82 may be changed by changing the pitch of the twist along its length. In one embodiment, element 82 is 15 cm (6 inches) long with a pitch length of about 4 mm (0.16 inch) along most of the length with a shorter twist, having a pitch length of about 2 mm (0.08 inch), along a segment about 3 cm (1.2 inches) long towards the center of element 82. Varying the twist also marks stop and start positions related to pre-deployment and post-deployment of braided tissue anchor 84. Other marking schemes, such as changes in color or texture, could also be used.

Figure 7:
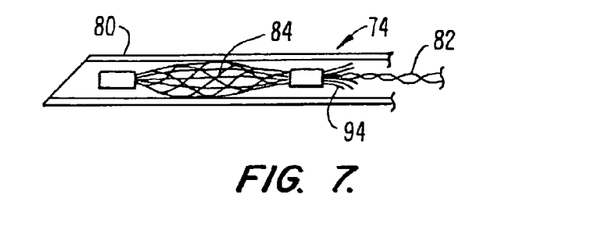
FIGS. 7 and 8 illustrate a strand-type movement limiting element made according to the invention.
Figure 8:
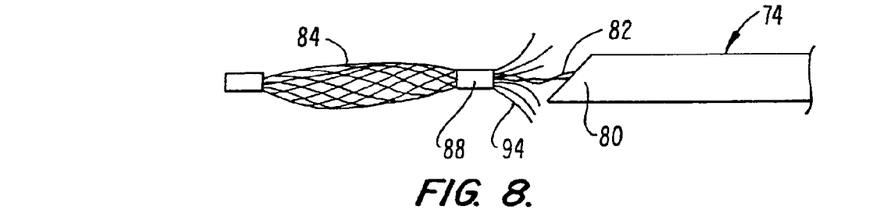
Figure 9:
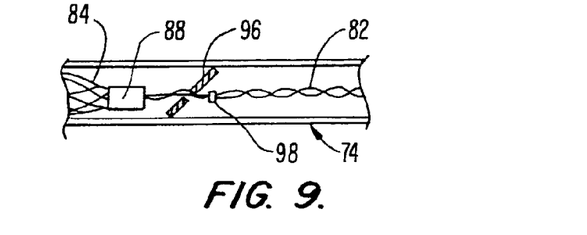
FIGS. 9–11 illustrate an oval disk-type movement limiting element.
Figure 10:
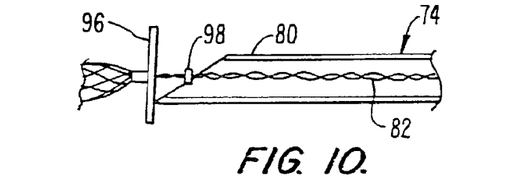
Figure 11:
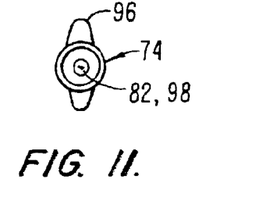
Figure 12:
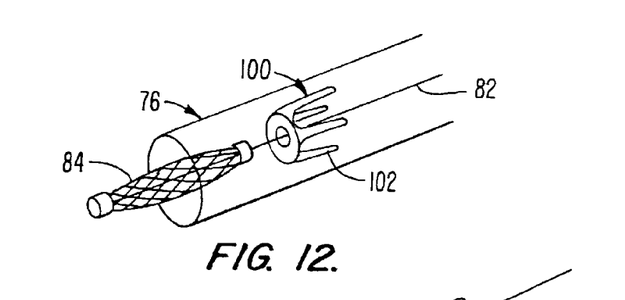
FIGS. 12–15 illustrate a fingered disk-type movement limiting element.
Figure 13:
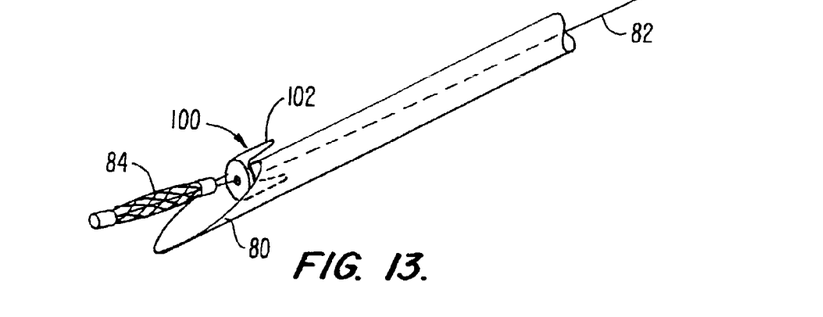
Figure 14:
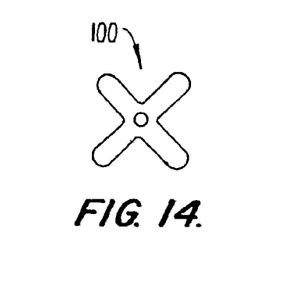
Figure 15:
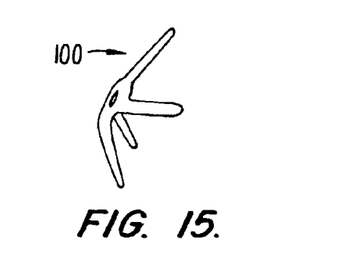

Once distal end 80 of anchor assembly 72 is properly positioned, tissue anchor 84 is extended out past distal end 80 as suggested in FIGS. 7 and 8. To move tissue anchor 84 from a radially contracted condition as shown in FIGS. 7 and 8, anchor actuator element 82 is pulled proximally causing tissue anchor 84 to move towards distal end 80 of placement element 74. However, tissue anchor 84 may be prevented from reentering distal end 80 of placement element 74 by various movement-limiting elements. One movement-limiting element is shown in FIGS. 7 and 8 in which tissue anchor 84 is made so that strands 94 of braided tissue anchor 84 to extend out from between sleeves 88, 90; strands 94 engage distal end 80 and prevent tissue anchor 84 from reentering distal end 80 of placement element 74. Another movement-limiting elements is shown in FIGS. 9, 10 and 11. In this embodiment an oval disk 96, having a hole through its center, is slidably mounted over anchor actuator element 82 and is free to slide between outer sleeve 88 and a keeper 98 secured to actuator element 82. Distal movement of actuator element 82 causes both tissue anchor 84 and disk 96 to move out from within placement element 74. However, once disk 96 is outside of placement element 74, its oval character prevents it from reentering placement element 74 so to permit tissue anchor 84 to be moved to its radially expanded condition. FIGS. 12–15 disclosed a further way of permitting tissue anchor 84 to be placed in its radially expanded condition. Instead of an oval disk 96, the movement-limiting elements may comprise the a fingered disk 100. Any attempt to pull tissue anchor 84 and fingered disk 100 therewith back into placement element 74 will cause or more of the fingers 102 of disk 100 to engage distal end 80 of placement element 74. This tendency to engage distal end 80 may be increased by making fingers 102 of a resilient material tending spring outwardly once no longer restrained within placement element 74 as suggested by FIGS. 14 and 15. Other movement-limiting elements engageable between placement element 74 and a proximal portion of tissue anchor 84 may also be used.

Figure 16:
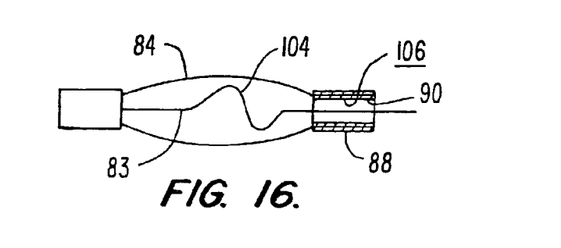
FIGS. 16–17 illustrate an anchor locking element used to at least temporarily maintain the tissue anchor in a radially expanded condition.
Figure 17:
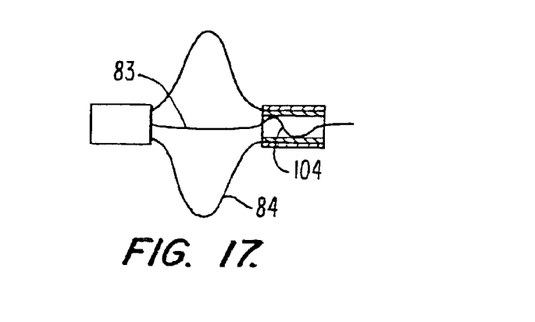
Figure 18:
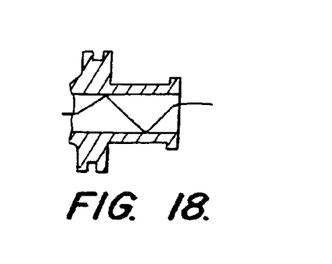
FIGS. 18–19 illustrate an alternative to the anchor locking element of FIGS. 16–17.
Figure 19:
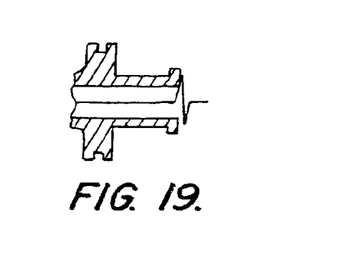

Once in a radially expanded condition, tissue anchor 84 may be retained in its radially expanded condition to various ways. One way is shown in FIGS. 16 and 17 in which single strand portion 83 of anchor element 82 has a sine wave shaped bent portion 104 sized and positioned to frictionally engage the inner surface 106 of inner sleeves 90 when tissue anchor 84 is in the radially expanded condition of FIG. 17. Other structure for at least temporarily preventing collapse of tissue anchor 84, such as using pre-shaped, shape memory wire section 108 of anchor element 82 as seen in FIGS. 18 in 19, could be used.

Modification and variation may be made to be disclosed embodiments without departing from the subject of the invention that defined in the following claims. For example, anchor 18 may be temporarily maintained in its expanded, deployed condition by using other structures or methods to keep wire 16 from passing back into shaft 14, such as winding wire 16 about a spindle or crimping a removable or permanent keeper onto wire 16 adjacent to proximal end 46 of shaft 14. In some situations handle 36 and/or sheath assembly 24 may not be needed. In some cases it may be desired to construct anchor 18 so that once in the radially expanded, deployed condition, it may not be placed in a radially contracted condition; in such cases it may be desirable to collapse the anchor by pulling it into the open distal end of an introducer sheath, which may or may not have a larger internal diameter than sheath 26. While the present invention is especially suited for use within the breast, it may be used within other regions of the body.

Any and all patents, patent applications and printed publications referred to above are incorporated by reference.

What is claimed is:

1. A target tissue localization assembly comprising:
   an anchor assembly comprising:
      an elongated placement element having a placement element distal end and a placement element proximal end;
      an elongated anchor actuator element comprising a wire and having an actuator element distal end and an actuator element proximal end, extending along the placement element, the actuator element distal end movable relative to the placement element distal end;
      and a radially expandable tissue anchor operably coupleable to the placement and anchor actuator elements, movable from a radially contracted condition to a radially expanded, deployed condition when the distal ends are moved relative to one another from a first state to a second state; and
      a lock engageable between the actuator element and the placement element when the anchor is in the deployed condition to at least temporarily prevent collapse of the anchor by preventing movement of the distal ends back to the first state.

2. The assembly according to claim 1 wherein the anchor is connected to the distal ends of the placement and anchor actuator elements.

3. The assembly according to claim 1 further comprising a sheath slidably mounted over the anchor assembly.

4. The assembly according to claim 1 wherein the placement element comprises a hollow shaft.

5. The assembly according to claim 1 wherein the placement element is stiff.

6. The assembly according to claim 1 wherein the anchor comprises a tubular mesh tissue anchor.

7. The assembly according to claim 1 wherein the anchor is an axially collapsible, radially expandable anchor.

8. The assembly according to claim 7 wherein the anchor is movable from the radially contracted condition to the radially expanded, deployed condition when the distal ends are moved toward one another.

9. The assembly according to claim 1 further comprising the sheath assembly, said sheath assembly comprising:
a sheath, having proximal and distal ends, slidably mounted over the anchor assembly; and
a hub mounted to the proximal end of the sheath.

10. The assembly according to claim 1 further comprising:
a sheath slidably mounted over the anchor assembly;
a chosen one of the placement element and the sheath comprising a surface interruption at a first location along said chosen one;
the other of the placement element and the sheath comprising a surface interruption engagement element at a second position along said other; and
the surface interruption element and the surface interruption engagement element being configured to (a) permit the surface interruption engagement element to move past the surface interruption in a first direction but (b) not permit the surface interruption engagement element to move past the surface interruption in a second direction opposite the first direction.

11. The assembly according to claim 10 wherein said sheath comprises a hub, said surface interruption comprises a shoulder defined by a groove formed in the placement element, and said surface interruption engagement element comprises a clip carried by the hub, said clip comprising a spring finger which frictionally engages said placement element and permits the hub to move in a proximal direction past said shoulder while preventing the hub from moving past the shoulder in a distal direction.

12. The assembly according to claim 1 wherein the lock has a first surface and the placement element has a second surface, the first surface movable to a stable engagement position contacting the second surface when the anchor is in the deployed condition.

13. The assembly according to claim 12 wherein said placement element defines an axis and the first and second surfaces engage along a plane at an acute angle to said axis.

14. The assembly according to claim 1 further comprising a handle housing the lock.

15. The assembly according to claim 14 wherein said handle is removable; thereby exposing the lock when the anchor is in the deployed condition and the first and second surfaces are engaged.

16. The assembly according to claim 1 wherein said anchor is effectively fully radially expanded when in the deployed condition.

17. The assembly according to claim 1 further comprising a protective cover, having a hollow cover interior, removably covering the placement element proximal end.

18. The assembly according to claim 17 wherein the placement element comprises a hollow tubular placement element and the protective cover has a fluid coupling so to permit fluid to be introduced through the fluid coupling, through the hollow cover interior and through the hollow tubular placement element.

19. A target tissue localization assembly comprising:
an elongated placement element having a placement element distal end and a placement element proximal end;
an elongated anchor actuator element having an actuator element distal end and an actuator element proximal end, extending along the placement element, the actuator element distal end movable relative to the placement element distal end;
a radially expandable tissue anchor having a distal anchor portion connected to the distal end of the anchor actuator element and a proximal anchor portion, at least a portion of the anchor positionable at an extended position relative to the distal end of the placement element;
a movement-limiting element engageable between the placement element and the proximal anchor portion when at said extended position so to at least hinder proximal movement of the proximal anchor portion when said actuator element is pulled proximally to permit radial expansion of the anchor to a deployed condition; and
locking means for at least temporarily preventing collapse of the anchor when the anchor is in the deployed condition.

20. The assembly according to claim 19 wherein the placement element comprises a stiff hollow shaft, said stiff hollow shaft constituting an introducer sheath.

21. The assembly according to claim 19 wherein the movement-limiting element is engageable between the distal end of the placement element and the proximal anchor portion.

22. The assembly according to claim 19 wherein the anchor actuator element comprises a flexible wire.

23. The assembly according to claim 19 wherein the anchor comprises an inner surface at said proximal anchor portion and the locking means comprises an element which frictionally engages the inner surface when the anchor is in the deployed condition.

24. The assembly according to claim 19 wherein said movement-limiting element extends radially outwardly and longitudinally proximally from the proximal anchor portion so to engage the placement element distal end.

25. The assembly according to claim 19 further comprising a protective cover, having a hollow cover interior, removably covering a proximal end of the placement element.

26. The assembly according to claim 25 wherein the placement element comprises a hollow tubular placement element and the protective cover has a fluid coupling so to permit fluid to be introduced through the fluid coupling, through the hollow cover interior and through the hollow tubular placement element.

27. The assembly according to claim 19 wherein the anchor actuator element comprises a wire.

28. The assembly according to claim 27 wherein the wire comprises a flexible twisted wire.

29. The assembly according to claim 19 wherein the anchor comprises a tubular mesh tissue anchor.

30. The assembly according to claim 19 wherein the anchor is an axially collapsible, radially expandable anchor.

31. The assembly according to claim 30 wherein the anchor is movable from a radially contracted condition to a radially expanded, deployed condition when the distal and proximal anchor portions are moved toward one another.

32. A method for localizing target tissue at a target site of a patient comprising:
percutaneously positioning a tip of an anchor assembly at or near a target site of a patient, the anchor assembly comprising;
an elongated placement element;
an elongated anchor actuator element comprising a wire and extending along the placement element; and
a radially expandable tissue anchor operably coupled to the placement and anchor actuator elements;
placing the anchor in a radially expanded condition by moving at least portions of the anchor actuator and placement elements relative to one another in a first direction; and
at least temporarily preventing movement of said portions of the anchor actuator and placement elements relative to one another in a second direction opposite said first direction thereby maintaining the anchor in the radially expanded condition.

33. The method according to claim 32 wherein the tip positioning step is carried out at a target site within a breast of a patient.

34. The method according to claim 32 wherein the placing step is carried out by:
positioning the tip at the target site;
moving the anchor assembly in a distal direction so to position the tip at a first distal position;
expanding the anchor to its radially expanded condition; and
said moving and expanding steps carried out so that the radially expanded anchor is at the target site when in its radially expanded condition.

35. The method according to claim 32 wherein the placing step comprises grasping a handle, the handle engaging a proximal portion of the actuator element, pushing the handle and the actuator element therewith in a distal direction to a distal position, and then pulling the handle and the actuator element therewith in a proximal direction from the distal position to a proximal position.

36. The method according to claim 35 further comprising separating the handle from the anchor assembly.

37. The method according to claim 32 wherein the tip positioning step takes place with the anchor assembly slidably housed within a sheath assembly.

38. The method according to claim 37 further comprising:
maintaining the sheath assembly at a fixed position relative to the patient following the positioning step; and
preventing proximal movement of the placement element relative to the sheath assembly.

39. The method according to claim 32 wherein said sheath is moved proximally when moved in said first direction and said sheath is move distally when moved in said second direction.

40. A target tissue localization assembly comprising:
an anchor assembly comprising:
an elongated placement element;
an elongated anchor actuator element extending along the placement element; and
a radially expandable tissue anchor operably coupleable to the placement and anchor actuator elements so to move from a radially contracted condition to a radially expanded condition when at least portions of the anchor actuator element and the placement element are moved relative to one another;
a sheath slidably mounted over the anchor assembly;
a chosen one of the placement element and the sheath comprising a surface interruption at a first location along said chosen one;
the other of the placement element and the sheath comprising a surface interruption engagement element at a second position along said other; and
the surface interruption element and the surface interruption engagement element being configured to (a) permit the surface interruption engagement element to move past the surface interruption in a first direction but (b) not permit the surface interruption engagement element to move past the surface interruption in a second direction opposite the first direction.

41. The assembly according to claim 40 wherein said sheath comprises a hub, said surface interruption comprises a shoulder defined by a groove formed in the placement element, and said proximal direction past said shoulder while preventing the hub from moving past the shoulder in a distal direction.

42. The assembly according to claim 40 wherein the placement and anchor actuation elements have distal ends, and the anchor is connected to the distal ends of the placement and anchor actuator elements.

43. The assembly according to claim 40 wherein the placement element comprises a hollow shaft.

44. The assembly according to claim 40 wherein the placement element is stiff.

45. The assembly according to claim 40 wherein the anchor actuator element comprises a wire.

46. The assembly according to claim 40 wherein the anchor comprises a tubular mesh tissue anchor.

47. The assembly according to claim 40 wherein the anchor is an axially collapsible, radially expandable anchor.

48. The assembly according to claim 47 wherein the placement and anchor actuator elements have distal ends, and the anchor is movable from the radially contracted condition to the radially expanded condition when the distal ends are moved toward one another.

49. The assembly according to claim 40 wherein said anchor is effectively fully radially expanded when in the deployed condition.

50. The assembly according to claim 40 further comprising a protective cover, having a hollow cover interior, removably covering a proximal end of the placement element.

51. The assembly according to claim 50 wherein the placement element comprises a hollow tubular placement element and the protective cover has a fluid coupling so to permit fluid to be introduced through the fluid coupling, through the hollow cover interior and through the hollow tubular placement element.

52. A method for localizing target tissue at a target site of a patient comprising:
percutaneously positioning a tip of an anchor assembly, slidably housed within a sheath assembly, at a target position relative to a target site of a patient, the anchor assembly comprising;
an elongated placement element;
an elongated anchor actuator element extending along the placement element said anchor actuator element comprising the tip; and
a radially expandable tissue anchor connected to the placement and anchor actuator elements;
maintaining the sheath assembly at a fixed position relative to the patent following the positioning step;
sliding the placement element distally within the sheath assembly from a first position to a second position;

preventing proximal movement of the placement element relative to the sheath assembly froze the second position to the first position; and placing the anchor in a radially expanded condition by moving the anchor assembly relative to the placement element.

53. The method according to claim 52 wherein the tip positioning step is carried out at a target site within a breast of a patient.

54. The method according to claim 52 wherein the placing step is carried out by:

positioning the tip at the target site;

moving the anchor assembly in a distal direction so to position the tip at a first distal position;

expanding the anchor to its radially expanded condition; and said moving and expanding steps carried out so that the radially expanded anchor is at the target site when in its radially expanded condition.

* * * * *